(12) United States Patent
Heald et al.

(10) Patent No.: US 9,089,648 B2
(45) Date of Patent: Jul. 28, 2015

(54) MEDICATED MODULE WITH PREMIX MEDICAMENT

(75) Inventors: Michael James David Heald, Maidenhead (GB); Christopher James Smith, Crewe (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 447 days.

(21) Appl. No.: 13/375,720
(22) PCT Filed: Jun. 1, 2010
(86) PCT No.: PCT/EP2010/057576
§ 371 (c)(1),
(2), (4) Date: Jan. 25, 2012
(87) PCT Pub. No.: WO2010/139669
PCT Pub. Date: Dec. 9, 2010

(65) Prior Publication Data
US 2012/0116349 A1 May 10, 2012

Related U.S. Application Data

(60) Provisional application No. 61/183,463, filed on Jun. 2, 2009.

(30) Foreign Application Priority Data

Jul. 25, 2009 (EP) ..................................... 09009659

(51) Int. Cl.
*A61M 5/24* (2006.01)
*A61M 5/32* (2006.01)
(Continued)

(52) U.S. Cl.
CPC ........... *A61M 5/2448* (2013.01); *A61M 5/2466* (2013.01); *A61M 5/32* (2013.01);
(Continued)

(58) Field of Classification Search
CPC ... A61M 5/2448; A61M 5/2466; A61M 5/32; A61M 5/3294; A61M 2005/1787; A61M 5/31525; A61M 5/347; A61M 2206/20; A61M 5/31573
USPC .......... 604/207, 208, 82–92, 151, 65–67, 506
See application file for complete search history.

(56) References Cited

U.S. PATENT DOCUMENTS 3,563,240 A 2/1971 Silver
3,908,654 A 9/1975 Lhoest et al.
(Continued)

FOREIGN PATENT DOCUMENTS

CN 2703534 Y 6/2005
JP H01-500803 A 3/1989
(Continued)

OTHER PUBLICATIONS

Japanese Patent Application No. 2012-513582, Office Action dated May 27, 2014.

*Primary Examiner* — Manuel Mendez
(74) *Attorney, Agent, or Firm* — McDonnell Boehnen Hulbert & Berghoff LLP (57) ABSTRACT

A medicated module (4) for an injection system to co-deliver at least two medicaments (1, 2) is disclosed where a primary delivery device (7) contains a first drug agent and accepts a medicated module (4) containing a single dose of a secondary premix medicament (2) containing the first drug agent and at least a second drug agent, where both the primary medicament (1) and the secondary premix medicament (2) are delivered through a single hollow needle (3, 16, 21, 31).

20 Claims, 4 Drawing Sheets (51) Int. Cl.
  *A61M 5/315* (2006.01)
  *A61M 5/34* (2006.01)
  *A61M 5/178* (2006.01)
(52) U.S. Cl.
  CPC ........ *A61M 5/3294* (2013.01); *A61M 5/31525* (2013.01); *A61M 5/31573* (2013.01); *A61M 5/347* (2013.01); *A61M 2005/1787* (2013.01); *A61M 2206/20* (2013.01)

(56) References Cited

U.S. PATENT DOCUMENTS

| | | | |
|---|---|---|---|
| 5,281,198 A * | 1/1994 | Haber et al. | 604/86 |
| 6,004,297 A * | 12/1999 | Steenfeldt-Jensen et al. | 604/207 |
| 6,562,002 B1 * | 5/2003 | Taylor | 604/82 |
| 8,496,621 B2 * | 7/2013 | Basso et al. | 604/151 |
| 2002/0007142 A1 | 1/2002 | Hjertman et al. | |
| 2008/0114304 A1 | 5/2008 | Nalesso et al. | |
| 2008/0294100 A1 | 11/2008 | de Costa et al. | |
| 2009/0093792 A1 | 4/2009 | Gross et al. | |

FOREIGN PATENT DOCUMENTS

| | | |
|---|---|---|
| JP | 2005-532128 A | 10/2005 |
| JP | 2008-526300 A | 7/2008 |
| WO | 88/02265 A1 | 4/1988 |
| WO | 03000317 A1 | 1/2003 |
| WO | 2004/007002 A1 | 1/2004 |
| WO | 2006/073505 A2 | 7/2006 |
| WO | 2008140737 A2 | 11/2008 |

* cited by examiner

MEDICATED MODULE WITH PREMIX MEDICAMENT

CROSS REFERENCE TO RELATED APPLICATIONS

The present application is a 35 U.S.C. 371 National Application of PCT/EP2010/057576 filed Jun. 1, 2010, which claims priority to U.S. Provisional Patent Application No. 61/183,463 filed Jun. 2, 2009 and European Patent Application No. 09009659.5 filed Jul. 25, 2009, the entire contents of which are incorporated entirely herein by reference.

FIELD OF THE PRESENT PATENT APPLICATION

This disclosure relates to medical devices and methods of delivering at least two drug agents from separate reservoirs using devices having only a single dispense interface. A single delivery procedure initiated by the user causes a non-user settable dose of a second drug agent and a variable set dose of a first drug agent to be delivered to the patient. Our invention is specifically directed to a medicated module having a premix of at least two drug agents, where one of the drug agents is the same as found in an attached drug delivery device. Our invention is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two or more active medicaments or "agents" simultaneously. The two or more active agents may interact with each other during the long-term, shelf life storage of the formulation. A formulation comprising at least two active agents will preferably be understood as pre-mix/premix medicament or pre-mixed/premixed formulation in the context of this disclosure. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more active agents may require a titration period to gradually introduce a patient to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. The present application discloses specific embodiments of methods, devices and drug delivery systems that overcome the above-mentioned concerns by providing separate storage containers for two or more active drug agents that are then only combined and/or delivered to the patient during a single delivery procedure. Setting a dose of one medicament automatically fixes or determines the dose of the second medicament (i.e., a non-user settable dose).

According to the disclosure the term medicated module is preferably used to characterize a containment or reservoir of a (secondary) drug compound within a needle sub-assembly. As such a medicated module may comprise at least one double ended needle. Furthermore a medicated module may comprise a needle guard and/or a bypass. The bypass can be any configuration, such as, a channel, pipe, conduit, groove, slot, or any other like pathway that is capable of carrying the medicament from the primary reservoir (e.g. cartridge) to the second needle or output needle without communicating with the secondary reservoir/medicament Moreover, the opportunity may be given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of a secondary medicament. The user or healthcare professional would then select the most appropriate secondary package or series or combination of series of different packages for a particular treatment regime.

In situations where a primary medicament is used to push or flush out a secondary medicament from a separate package or reservoir, the volume of the secondary medicament in the reservoir will offset the absolute volume of the actual dose of the primary medicament that is delivered from the delivery device. Obviously, a given volume or set dose of medicament can contain a variety of concentrations of one or more drug agents depending on the formulation protocol that was used to prepare the medicament. As such, although the user sets a specific dose A of the primary medicament, in actuality only C amount of primary medicament (volume A minus the volume B of reservoir) will be delivered to the user/patient. To overcome this problem a complex technical redesign of the delivery device would be required to deliver the complete dose A and also to indicate the correct quantity or concentration of delivered primary medicament to the user in all use scenarios (e.g. if the user were to take only the primary medicament, the device would have to be able to indicate the correct dialed and received dose). In specific embodiments, our invention solves this problem by premixing the secondary medicament in the secondary reservoir with a predetermined volume of the primary medicament. In one embodiment the predetermined volume of the primary medicament may be equal to the volume of the secondary reservoir. In a further embodiment the secondary reservoir may contain the same concentration of the primary drug as does the primary reservoir.

These and other advantages will become evident from the following more detailed description of the invention.

Problem to be Solved

The general problem to be solved by the present invention is to provide a medicated module, a drug delivery system and a method where the administration of a medicament is facilitated.

SUMMARY

The disclosed medicated module allows complex combinations of multiple drug compounds within a single drug delivery system. In particular, a user may be enabled to set and dispense a multi-drug compound device through one single dose setting mechanism and a single dispense interface. This single dose setter may control the mechanism of the device such that a predefined combination of the individual drug compounds is delivered when a single dose of one of the medicaments is set and dispensed through the single dispense interface. The term drug dispense interface preferably is, in the context of this disclosure, any type of outlet that allows the two or more medicaments to exit the drug delivery system and be delivered to the patient. In a preferred embodiment the single drug dispense interface comprises a hollow needle cannula.

By defining the therapeutic relationship between the individual drug compounds, our delivery device may help ensure that a patient/user receives the optimum therapeutic combination dose from a multi-drug compound device without the inherent risks associated with multiple inputs where the user has to calculate and set the correct dose combination every time they use the device. The combination of the individual medicaments comprises preferably at least two different drug agents, wherein each medicament comprises at least one drug agent. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, this invention may be of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a primary or master drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In specific embodiments, our invention solves the following problem. A user sets a dose of primary medicament on a delivery device to 30 units. In certain design embodiments, the primary compound is used to flush or push a secondary medicament from a reservoir having, for example, a 5 unit volume. Although the patient receives all 5 units of the secondary medicament, they will only receive 25 of the set 30 units of the primary medicament because 5 units of the primary medicament remain in the secondary reservoir. Therefore, the patient has not received their full dose of primary medicament even though the user set the correct dose, and the device will incorrectly indicate that the correct dose has been delivered.

By using a premix secondary medicament in an attachable medicated module, this allows the user to dial or set a dose of the primary medicament and know that this set dose will actually be delivered because the premix contains a known quantity of the primary medicament. Here, the secondary medicament can be dissolved in a volume of primary medicament equal to the secondary reservoir volume.

For example, if 20 µg of a drug X is dissolved in 50 mcl of solution in the drug reservoir (the solvent of which consists of drug Y at a concentration of 0.1 mcg/1 mcl (i.e. 5 mcg of drug Y in 50 mcl), then upon activation of a delivery device containing a primary reservoir of drug Y and a set dose of 30 mcg of drug Y (i.e. 300 mcl) then 300 mcl still displace/replace the 50 mcl of premix, but patient still receives the set dose of 30 mcg of drug Y and the 20 μg of drug X. In other words, although the secondary reservoir still retains 5 mcg of drug Y after dose delivery, this loss is counterbalanced by the 5 mcg (50 mcl) units of drug Y originally contained in the secondary reservoir that was used to dissolve drug X.

Another problem relates to the need to avoid diluting the drug in the primary container. The safety and efficacy of some drugs can be affected by the concentration of the drug in solution when administered to the patient. For example, as per the example above, drug Y in the primary container may have an optimal safety and efficacy profile at a concentration of 0.1 mcg/ml. If this concentration were to be delivered through the drug reservoir it would be diluted by the solution of drug X in the reservoir and its safety and efficacy might be affected. If instead the drug reservoir contains a pre-mix of drug X and Y (at a concentration of 0.1 mcg/ml), no dilution of drug Y will occur.

In one embodiment, our invention relates to a medicated module attachable to a drug delivery device. The medicated module may comprise a housing having a proximal end and a distal end, where the proximal end may be configured for attachment to the drug delivery device. In particular, the proximal end may have a connector configured for attachment to the drug delivery device. The medicated module comprises a reservoir containing at least one dose of a pre-mixed medicament. The reservoir may contain only a single dose of the medicament. At least one drug agent in the premix medicament is the same or an equivalent of a drug agent contained in a primary reservoir of a drug delivery device. In other words the medicated module contains a premixed medicament that comprises at least two different drug agents.

The reservoir may be located within the housing. In particular, the housing may comprise a recess that defines the reservoir. In a further embodiment, the reservoir may be defined by a section of a needle. The needle may be fixed within the housing.

In another embodiment, our invention relates to a medicated module attachable to a drug delivery device, comprising a housing having a proximal end and a distal end, where the proximal end has a connector configured for attachment to a drug delivery device, which houses a primary reservoir containing of a first medicament. The drug delivery device may be a multi-dose device, wherein the primary reservoir contains multiple doses of the first medicament. The module has a double-ended needle fixed within the housing, where the needle has an enlarged section between the two ends that defines a second reservoir. The secondary reservoir contains a single dose of a second medicament comprising a premix of the first medicament with at least one different medicament. The first needle is configured for fluid communication with the primary reservoir when the medicated module is attached to the drug delivery device.

In another embodiment the medicated module has a housing having a proximal end and a distal end, where the proximal end has a connector configured for attachment to a drug delivery device that has a primary reservoir containing multiple doses of a first medicament. A first needle is fixed within a seal in the proximal end of the housing and a second needle is fixed within the distal end of the housing. A recess is located within the housing that defines a second reservoir that is in fluid communication with the second needle and the seal. The recess contains a single dose of a second medicament comprising a drug agent that is the same as at least one of the drug agents in the primary reservoir. The first needle is configured for fluid communication with the primary reservoir when the medicated module is attached to the drug delivery device.

In yet another embodiment the medicated module has a first needle fixed within a retention cap inside the module housing and a second needle fixed within the distal end of the housing. A recess located within the housing and beneath the retention cap defines a second reservoir that is in fluid communication with the first and second needles. Inside the reservoir is at least one spiral manifold that contains a single dose of a second medicament comprising a drug agent that is the same as at least one of the drug agents in the primary reservoir. In a more preferred embodiment, the second reservoir contains two or more spiral manifolds positioned in a stacked arrangement.

Yet another embodiment covers a medicated module where a first needle is fixed within a retention cap positioned in the proximal end of the housing. A second needle is fixed within the distal end of the housing. A second reservoir having top and bottom seals configured for fluid engagement with the first and second needle contains a single dose of a second medicament comprising a drug agent that is the same as at least one of the drug agents in the primary reservoir. The retention cap has retention features engaging the second reservoir. In a more preferred embodiment, the first and second needles pierce the top and bottom seals, respectively, when the medicated module is attached to the drug delivery device. Preferably, the second reservoir is aseptically sealed in a separate container or capsule. The retention cap is preferably configured to move axially in the distal direction when the medicated module is attached to the drug delivery device.

In some cases where priming of the drug delivery system is desirable, the medicated module has a bypass to allow medicament from the primary reservoir to flow around the secondary reservoir and exit the second needle. The bypass can be any configuration, such as, a channel, pipe, conduit, groove, slot, or any other like pathway that is capable of carrying the medicament from the primary reservoir to the second needle without communicating with the secondary reservoir/medicament. The advantage of such a bypass allows the multi-use device to be primed and also both the primary and secondary needles to be primed without expelling any of the volume of the secondary medicament. In this case, the seals of the secondary reservoir may be pierced after priming to allow injection of both the primary and secondary medicament. Alternatively, the bypass channel may be used to inject only the primary medicament. One preferred configuration of the bypass comprises a channel or a groove in the module housing that allows medicament from the primary reservoir to flow around a capsule or contained reservoir containing the second medicament.

Moreover, a method of dispensing at least two medicaments from separate reservoirs is disclosed. The method comprises the steps of providing a drug delivery device comprising a device housing containing a dose button operably connected to a primary reservoir of medicament containing at least a first drug agent and providing a medicated module configured for attachment to the drug delivery device. The medicated module comprises a reservoir containing at least one dose of a premix medicament containing the first drug agent and at least a second drug agent. The reservoir may contain only a single dose of a medicament. As an example, the reservoir may be located within a housing of the medicated module. The module has mounted therein at least one needle. A single activation of the dose button causes medicament from the primary reservoir and at least one dose of the premix medicament to be expelled through the needle.

Moreover, a method of dispensing a fixed dose of one medicament and a variable dose (user settable) of a primary or first medicament from separate reservoirs is disclosed that involves the steps of first setting a dose of a first medicament contained in a primary reservoir of a drug delivery device having a single dose setter. By user settable dose it is meant dose that the user (user or health care provider) can physically manipulate the device to set a desired dose. Likewise, the user settable dose can be set remotely through the use of wireless communication (Bluetooth, WiFi, satellite, etc.) or the dose could be set by another integrated device, such as a blood glucose monitor after performing a therapeutic treatment algorithm. Next a dose button is activated that moves the set dose of the first medicament from the primary reservoir in a distal direction and simultaneously forcing substantially all of a non-user set dose (e.g. a single dose) of a premixed medicament from a secondary reservoir contained in a medicated module, such as those previously described, through a single dispense interface, preferably a hollow injection needle. The method of delivery of the medicaments could be simultaneous or sequential, or a combination of both. Upon completion of the delivery procedure substantially all of the premixed medicament has been expelled as well as the set dose of the first medicament through the single dispense interface. By "substantially all" we mean that at least about 80% of the second medicament is expelled from the drug delivery device, preferably at least about 90% is expelled. In one arrangement, preferably at least about 80% is delivered.

In a further embodiment, our invention is directed to a drug delivery system to deliver two or more medicaments operable through a single dispense interface that comprises a primary reservoir of medicament containing at least one drug agent. A dose button is operably connected to the primary reservoir of medicament. The single dispense interface is configured for fluid communication with the primary reservoir and with a secondary reservoir of medicament containing at least one drug agent. A single activation of the dose button causes medicament from the primary reservoir and at least one dose of the premix medicament from the secondary reservoir to be expelled through the drug dispense interface. The drug delivery system may comprise a housing containing a single dose setter operably connected to the primary reservoir.

The primary reservoir of the drug delivery system may be in fluid communication with the secondary reservoir. Here, the activation of the dose button may cause medicament from the primary reservoir flow into the secondary reservoir and thereby push out premix medicament from the secondary reservoir.

In yet another embodiment, our invention is directed to an injection device where the containment of a secondary premix medicament is within a needle sub-assembly (medicated module) designed for attachment to an associated primary or master delivery device. The actuation of the master device actuates the dispense of the secondary premix medicament and a primary compound contained in a reservoir in the master drug delivery device. The combination of compounds as discrete units or as a mixed unit is delivered to the body via an integral needle. This would provide a combination drug injection system that, from a user's perspective, would be achieved in a manner that very closely matches the currently available injection devices that use standard needles. One possible delivery procedure would involve the following steps:

1. Attach the medicated needle module to the distal end of the primary injection device (e.g. a threaded hub of a cartridge holder containing a 3 ml cartridge of the primary drug compound) such that the proximal end of the medicated needle is in fluidic communication with the primary compound.
2. Dial up/set the primary injection device such that it is ready to dispense the desired dose of the primary compound.
3. Insert the distal end of the medicated needle into the desired injection site. In some designs, insertion of the medicated needle can trigger delivery of the secondary compound.
4. Dose the primary compound by activating a dose button. This may also cause the secondary compound to automatically dispense.
5. Remove and dispose of the medicated needle module.

The medicated module of our invention can be designed for use with any drug delivery device with an appropriate compatible interface. However, it may be preferable to design the module in such a way as to limit its use to one exclusive primary drug delivery device through employment of dedicated or coded features to prevent insertion of a non-appropriate medicated module to a non-matching injection device. In some situations it may be beneficial from a therapeutic and safety point of view to ensure that the medicated module is exclusive to one drug delivery device (or family of devices) while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound in a way that would prevent the potential risk of double dosing of the secondary compound. A particular benefit of our invention is that the premixed secondary medicament negates the need for a complex primary device dose dispensation calculation system being aware of whether a combined or non-combined dose is being dispensed in order to indicate the correct dose information to the user.

A further particular benefit of the disclosed medicated module may be that it makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a user could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

A drug delivery device preferably comprises a primary reservoir of medicament containing at least one drug agent, a dose setter, a dose button, and a delivery mechanism. The dose button is operably connected to the primary reservoir. The dose setter is operably connected to the primary reservoir. The delivery mechanism may be of any type, e.g. the drive mechanism may utilize a rotatable piston rod, preferably a rotatable piston rod with two distinct threads.

In a preferred embodiment of our invention, the primary drug delivery device is used more than once and therefore is multi-use. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the user attempt to reuse a previously used medicated module, our invention could include features that could alert the user to this situation. Such means of alerting the user may include some (or all) of the following:
1. Physical prevention of medicated module re-attachment to the primary drug deliver device once the module has been used and removed.
2. Physical prevention of insertion of the used drug dispense interface into the patient (e.g. a single use needle-guard type arrangement).
3. Physical/hydraulic prevention of subsequent liquid flow through the drug dispense interface once it has been used
4. Physical locking of the dose setter and/or dose button of the primary drug delivery device.
5. Visual warnings (e.g. change in color and/or warning text/indicia within an indication window on the module once needle insertion and/or fluid flow has occurred).
6. Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections.

This convenience benefit may also result in improved compliance with the prescribed therapy, particularly for users who find injections unpleasant or who have computational or dexterity difficulties.

Our invention also covers a method of delivering two medicaments stored in separate packages. Preferably, the medicaments may both be liquid, or alternatively one or more of the medicaments may be a suspension or slurry. Most preferably, the primary package or reservoir contains insulin and the secondary package contains a premix comprising insulin and a glucagon-like peptide-1 (GLP-1), which is derived from the transcription product of the proglucagon gene.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
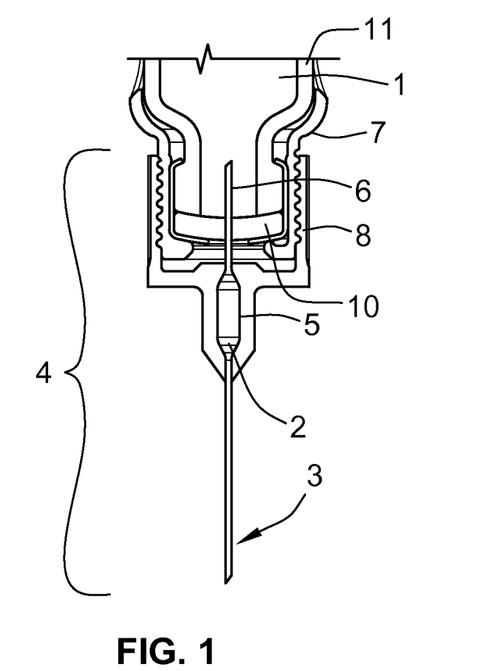
FIG. 1 illustrates an embodiment of the medicated module of the present invention having an enlarged needle portion attached to a drug delivery device.
Figure 2:
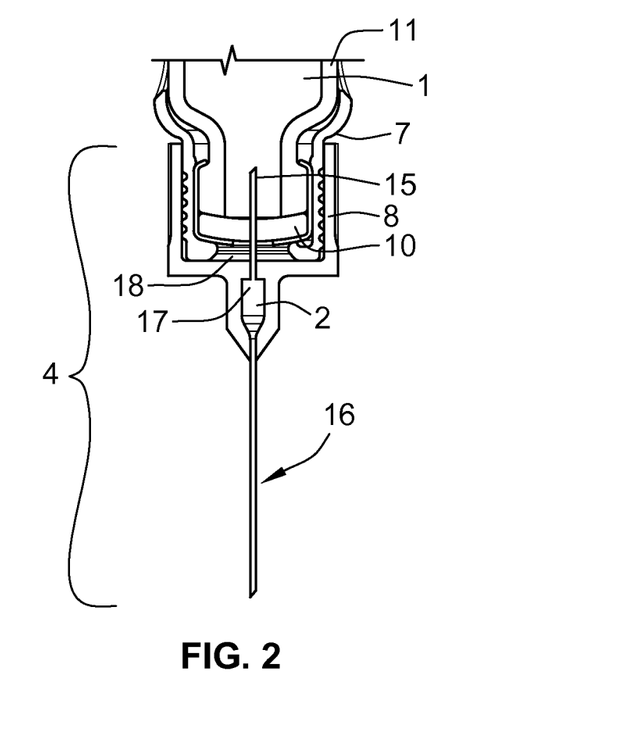
FIG. 2 illustrates an embodiment of the medicated module of the present invention having two needles connected to a secondary reservoir attached to a drug delivery device.
Figure 3:
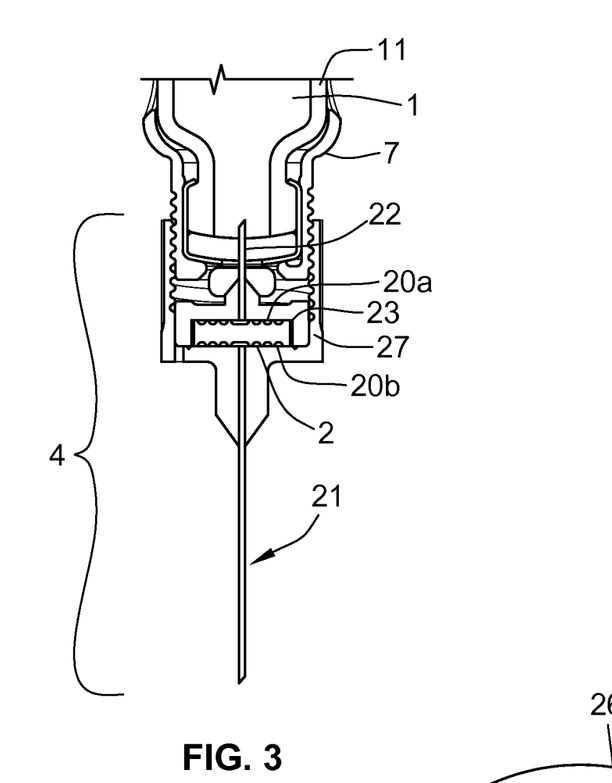
FIG. 3 illustrates an embodiment of the medicated module of the present invention having one or more spiral manifolds as part of the secondary reservoir attached to a drug delivery device.

Specific embodiments of the disclosed drug delivery device enables administering a fixed predetermined dose of a second medicament (secondary drug compound) and a variable dose of a first medicament (primary drug compound) through a single output or drug dispense interface. Setting the dose of the primary medicament by the user may automatically determine the fixed dose of the second medicament, which preferably is a single dose. In a preferred embodiment the drug dispense interface is a needle cannula (hollow needle). FIGS. 1-3 illustrate three different embodiments of our invention, each having a medicated module 4 attached to a drug delivery device 7. Each module is preferably self-contained and provided as a sealed and sterile disposable module that has an attachment means 8 compatible to the attachment means at the distal end of device 7. Although not shown, the medicated module could be supplied by a manufacturer contained in a protective and sterile container where the user would peel or rip open a seal or the container itself to gain access to the sterile medicated module. In some instances it might be desirable to provide two or more seals for each end of the medicated module.

Figure 8:
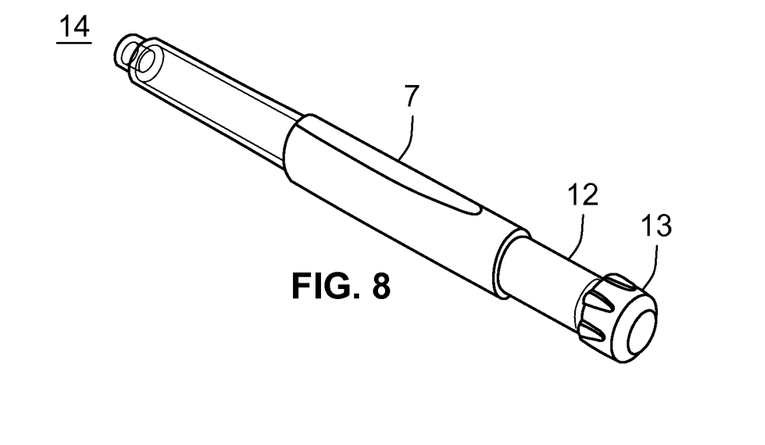
FIG. 8 illustrates one possible drug delivery device that can be used with the present invention.

One example of a drug delivery device 7 is illustrated in FIG. 8. Any known attachment means can be used, including permanent and removable connection means. Threads, snap locks, snap fits, luer locks, bayonet, snap rings, keyed slots, and combinations of such connections can be used to attach module 4 to device 7. FIGS. 1-3 illustrate the attachment means 8 as screw threads. The embodiments shown in FIGS. 1-3 have the benefit of the second medicament 2 as a single dose being contained entirely within the cannula 3, hence minimizing the risk of material incompatibility between the second medicament and the materials used in the construction of the medicated module 4.

As shown in FIG. 1 a unique aspect of this embodiment is the method of construction of output needle 3, part of which has an enlarged cross-section 5 to accommodate the volume of the fixed (single) non-user settable dose medicament 2. Preferably a hydroforming or a swaging process will be utilized to form the enlarged cross-section 5 of the needle 3. Both tips of the needle are preferably not enlarged which is beneficial because it helps minimize both the physical and mental/emotional trauma associated with insertion of larger bore needles as well as minimizing the risk of compromising the sealing integrity of the septa of the primary medicament container (multiple piercing of this type of material with a relatively large gauge needle may increase the risk of 'coring').

To minimize the residual volume of the second medicament that might remain in the needle module or sub-assembly 4 at the end of the dispense operation caused by recirculation, the enlarged section 5 should be designed with fluid flow characterizing models. Preferably, the design of the medicated module 4 should ensure that at least about 80% of the second medicament is expelled through the distal end of needle 3, most preferably at least about 90% should be expelled. Ideally displacement of the first medicament 1 into the proximal end 6 of needle 3 will displace the second medicament 2 without substantial mixing of the two medicaments. Preferably this is accomplished by minimizing the diametric increase and careful design of the transition from the small cross sections of the needle 3 to the enlarged cross section 5. One alternative is to have the assembly/filling process set up so as to ensure that a "plug" of gas (e.g. air or an inert gas, such as nitrogen) is present in the upper section 6 of the needle (above the enlarged section 5) this may act to ensure that the first and second medicaments are kept separate from each other thereby help ensure sequential delivery by action of a virtual piston created by the plug of air. This plug may additionally help ensure that there is no opportunity for the primary and secondary medicaments to mix prior to dispense (i.e. if the medicated module is left in the attached position for an extended period of time prior to the injection action being undertaken.

Attachment of the medicated module 4 to the multi-use drug delivery device 7 causes the engagement needle 6 located in the module to penetrate the septum 10 of cartridge 11 of the multi-use device 7. Once the engagement needle has passed through the septum of the cartridge fluid connection is made between the first medicament 1 and the output needle 3. The dose of the multi-use device 7 is then set using a dose setter 12 (see FIG. 8) in the normal manner (e.g. by dialing out the appropriate number of units). Dispense of the medicaments is then achieved by subcutaneously injecting the medicaments via activation of a dose button 13 on device 7. The dose button of our invention can be any triggering mechanism that causes the dose of the first medicament that was set by the dose setter to move distally towards the distal end 14 of the device. In a preferred embodiment the dose button is operably connected to a spindle that engages a piston in the primary reservoir of the first medicament. In a further embodiment the spindle is a rotatable piston rod comprising two distinct threads.

Another embodiment of our invention is shown in FIG. 2 where a primary needle 15 pierces the septum 10 of the device cartridge 11 and a second needle 16 is used to subcutaneously inject the medicament. Located between the two needles is a recess 17 containing the secondary reservoir of the second medicament 2. The primary needle 15 is attached to a retention cap 18, which when inserted into the top of the recess 17 provides a fluid seal.

In another embodiment of our invention one or more spiral manifolds 20 are used as part of the secondary reservoir to store the second medicament and to minimize the risk of mixing occurring between the two medicaments during dispense. In minimizing the risk of mixing it is desirable to minimize the cross-sectional area perpendicular to the flow direction where the two medicaments come into contact with each other. While desirable to minimize the cross-sectional area of the flow channel, the effect of this in a standard needle arrangement would be to increase the length of the flow channel for a fixed volume of the second medicament. This can result in an excessive and unacceptable axial length of the medicated module. Using one or more spiral manifolds provides a fluid path of minimal cross-sectional area, sufficient length to store the second medicament, within an acceptable minimum axial package space.

Figure 4:
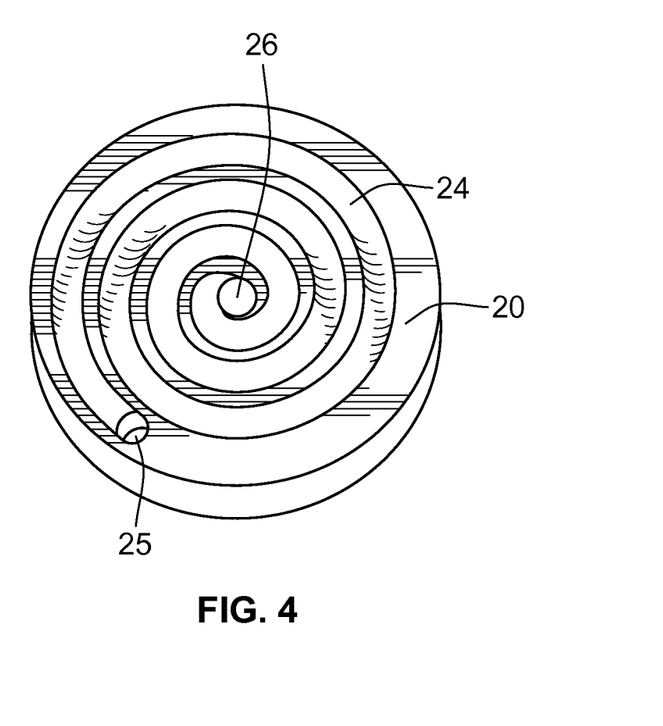
FIG. 4 illustrates a perspective view of an embodiment of one the spiral manifolds that make up part of the secondary reservoir attached to a drug delivery device.

Turning to FIG. 3, two spiral manifolds 20a & 20b (see FIG. 4) are utilized between the cartridge 11 of the reusable drug delivery device 7 and the output needle 21 to further reduce the axial package space of medicated module 4. The primary needle 22 attaches to a retention cap 23, which introduces the first medicament 1 to the center 26 of the first spiral manifold 20a. As the first medicament is dispensed into spiral manifold 20a, the second medicament 2 flows radially outward along the path of the spiral groove 24 until it reaches a predetermined radial position 25 whereby the flow path traverses through the first spiral manifold. Having passed through the spiral manifold the fluid path follows a second spiral orientated such that the fluid flows radially inward on the second spiral manifold 20b. As the fluid reaches the center of the second spiral manifold 20b fluid communication is made with the output needle 21 and the medicament is dispensed through the outlet needle to the patient.

In this embodiment it is anticipated that the spiral manifolds will have sealing features along the external edges of helical groove (not shown) and/or be made from a compliant material such as rubber, TPE, or like materials, and that the assembly of the retention cap 23 into the body or housing 27 of the medicated module will exploit these features to create a sealing labyrinth, thereby forming the helical flow channel.

Figure 5:
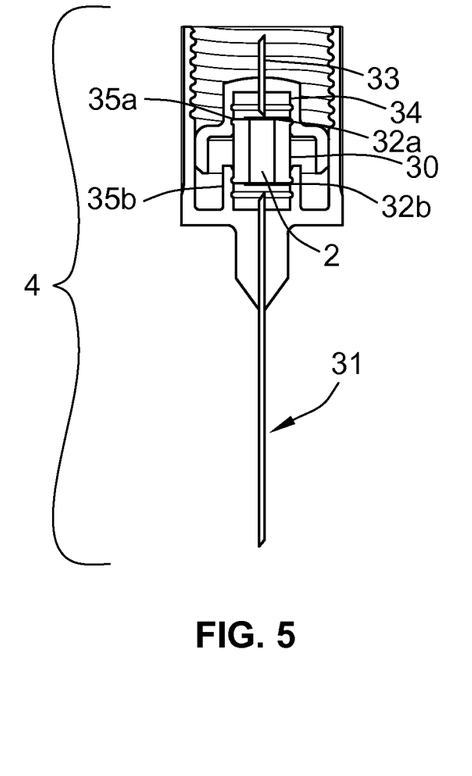
FIG. 5 illustrates an embodiment of the medicated module of the present invention having a self contained reservoir of secondary medicament having two pierceable membranes.
Figure 6:
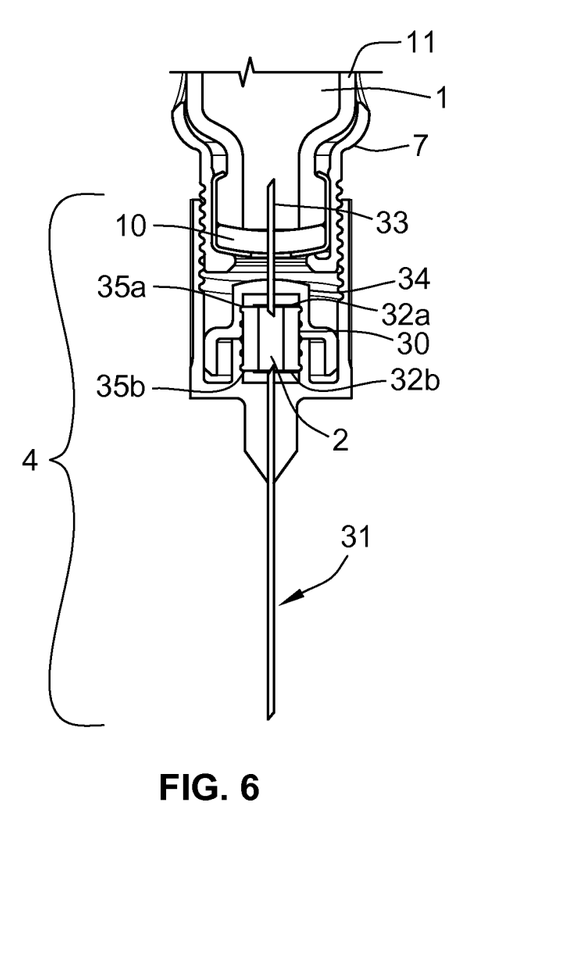
FIG. 6 illustrates an embodiment of the medicated module of the present invention having a self contained reservoir of secondary medicament having two pierceable membranes attached to a delivery device.
Figure 7:
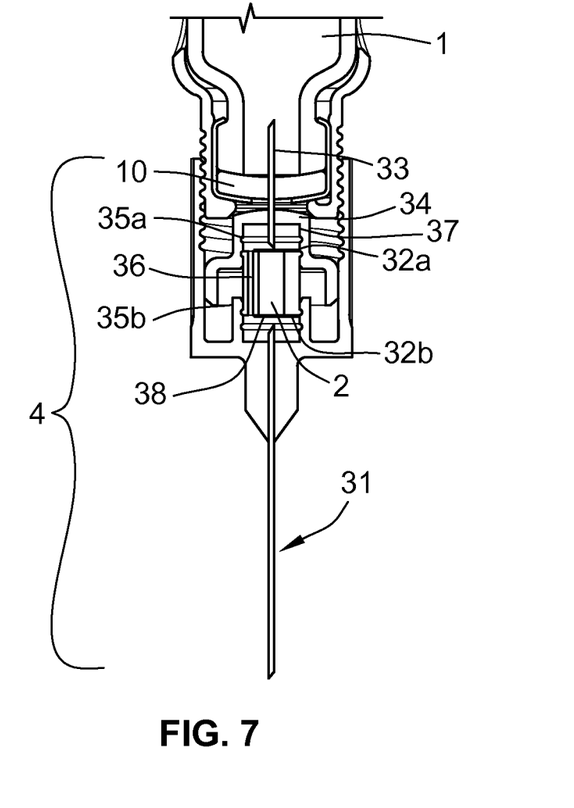
FIG. 7 illustrates an embodiment of the medicated module of the present invention having a self contained reservoir of secondary medicament having two pierceable membranes and a bypass channel.

Additional embodiments of our invention are illustrated in FIGS. 5, 6 & 7. In these embodiments the medicated module 4 contains a discrete secondary reservoir 30 containing a fixed single dose of the second medicament 2. As with the above embodiments these medicated modules administer a fixed predetermined dose of a second medicament and a variable dose of a primary medicament through a single output needle 31. As discussed in more detail below, FIG. 7 shows an alternative design of these embodiments that provides a priming feature using the primary medicament 1.

In the embodiments shown in FIGS. 5-7 reservoir 30 has ends that are sealed with pierceable membranes 32a and 32b that provides a hermetically sealed reservoir for the second medicament. A primary needle 33 can be displaced axially relative to the reservoir 30 such that in a depressed position the primary needle 33 will puncture the top membrane 32a. The output needle 31 protrudes above the lower surface of reservoir 30 and pierces the lower membrane 32b when the reservoir is moved axially relative to needle 31.

During use, on attachment of the medicated module to a multi-use drug delivery device, such as the one shown in FIG. 8, the primary needle 33 pierces septum 10 of cartridge 11 contained in device 7. This attachment causes the retention cap 34 to move distally a predetermined axial displacement so that the retention cap 34 bears against the cartridge causing the retention features 35a and 35b to be overcome and the primary needle to pierce the top membrane 32a of reservoir 30. Once the top of the reservoir bears against the retention cap the retention features holding the reservoir in the medicated module 4 are overcome and the reservoir moves axially downward. Axial movement of reservoir 30 causes the proximal end of output needle 31 to pierce lower membrane 32b of reservoir 30.

In any of the above described embodiments of our invention the second medicament may be either in a powdered solid state, any fluid state contained within the secondary reservoir or capsule, or coated to the inside surface of the drug dispense interface. According to a specific aspect of the present invention the second medicament comprises a premix comprising at least two drug agents, preferably the second medicament comprises a premix of two drug agents. In a preferred embodiment the premix second medicament comprises at least one drug agent that is the same or an equivalent of a drug agent contained in a primary reservoir of a drug delivery device. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

Yet another embodiment of our invention is shown in FIG. 7 where a bypass channel 36 is incorporated into reservoir 30 to facilitate priming of output needle 31 with the first medicament 1. When medicated module 4 of this embodiment is attached to a device, such as the one shown in FIG. 8, the primary needle 33 pierces septum 32a of reservoir 30, however, prior to the primary needle piercing the membrane the user has the option of initiating a priming operation utilizing bypass channel 36. This is achieved by dispensing the primary medicament into the cavity 37 between the retention cap 34 and the top pierceable membrane 32a. Since the cavity 37 is in fluid communication with bypass channel 36, the primary medicament flows around reservoir 30 and into lower cavity 38 and out through output needle 31. After the optional priming operation is complete the medicated module can be fully attached (rotated in the case of screw threads) to the multi-use device 7 causing the output and primary needles to pierce the lower and top membranes of the reservoir, respectively. Piercing of membranes 32a and 32b opens fluid communication between the first and second medicaments allowing them to be dispensed through operation of the dispense mechanism on the multi-use device. When this occurs bypass channel 36 is isolated from the contents of reservoir 30.

The connection or attachment between the medicated module of the above described embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The secondary reservoir or capsule may be manufactured from glass or other drug contact suitable material. The integrated injection needle can be any needle cannula suitable for subcutaneous or intramuscular injection. Additionally, the medicated module could incorporate a safety shield device that would prevent accidental needle sticks and reduces the anxiety experienced by users who suffer from needle phobia. The exact design of the safety shield is not critical to our invention, however, a preferred design is one that is operably connected to the first and/or second reservoirs. In such a design the activation of the safety shield could unlock the drug delivery system and in some cases cause the second medicament to be dispensed prior to activating the dose button to dispense the primary medicament from the first reservoir.

Preferably the medicated module is provided by a manufacture as a stand-alone and separate device that is sealed to preserve sterility. The sterile seal of the module is preferably designed to be opened automatically, e.g. by cutting, tearing or peeling, when the medicated module is advanced or attached to the drug delivery device by the user. This opening of the seal may be assisted by features such as angled surfaces on the end of the injection device or features inside the module.

The medicated module of our invention may be designed to operate in conjunction with a multiple use injection device, preferably a pen-type multi-dose injection device, similar to what is illustrated in FIG. 8. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A typical injection device contains a cartridge or another primary reservoir of first medication. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

In certain embodiments where the medicated module contains a single dose of a medicament, the module may have to be attached to a drug delivery device in order to administer the single dose in the reservoir to a patient. In other words, the medicated module may not be configured to be used as a stand-alone injection device. This is because the module does not have a dose delivery mechanism and instead relies on the dose delivery mechanism contained in the drug delivery device to which it must be attached.

Exemplary embodiments of the present invention have been described. Those skilled in the art will understand, however, that changes and modifications may be made to these embodiments without departing from the true scope and spirit of the present invention, which is defined by the claims.

LIST OF REFERENCES 1 first medicament
2 second medicament, premixed medicament
3 needle, cannula, output needle
4 medicated module
5 enlarged cross-section, enlarged section
6 section of needle/engagement needle, proximal end, upper section
7 drug delivery device
8 attachment means
10 septum
11 cartridge
12 dose setter
13 dose button
14 distal end of device
15 primary needle
16 second needle
17 recess
18 retention cap
20, 20a, 20b spiral manifolds
21 output needle
22 primary needle
23 retention cap
24 spiral groove
25 radial position
26 center of spiral manifold
27 body/housing of medicated module
30 secondary reservoir, reservoir
31 output needle
32a, 32b pierceable membrane/septum, membrane 33 primary needle
34 retention cap
35a, 35b retention features
36 bypass channel
37 cavity
38 lower cavity

We claim:

1. A medicated module attachable to a drug delivery device with a primary reservoir containing a first drug agent, comprising,
   a. a housing having a proximal end and a distal end, where the proximal end has a connector configured for attachment to a drug delivery device; and
   b. a secondary reservoir containing at least one dose of a premixed medicament, wherein at a point in time before the primary reservoir is fluidly connected to the second reservoir, a second drug agent contained in the premixed medicament is the same or an equivalent of the first drug agent contained in a primary reservoir of the drug delivery device.

2. The medicated module of claim 1, where the secondary reservoir is within the housing.

3. The medicated module of claim 1, comprising a double ended needle fixed within the housing, where the needle has a section that defines the reservoir.

4. The medicated module of claim 1, comprising,
   a. a first needle fixed within a hub in the proximal end of the housing;
   b. a second needle fixed within the distal end of the housing;
   c. a recess within the housing that defines the secondary reservoir that is in fluid communication with the second needle.

5. The medicated module of claim 1, comprising,
   a. a first needle fixed in a retention cap positioned in the proximal end of the housing;
   b. a second needle fixed within the distal end of the housing;
   wherein the secondary reservoir has top and bottom seals configured for fluid engagement with the first and second needles.

6. The medicated module of claim 1 where the secondary reservoir contains a single dose of the premixed medicament.

7. The medicated module of claim 1 wherein the first and second drug agents are of the same or of equivalent concentration.

8. The medicated module of claim 1 wherein the secondary reservoir is a sealed sterile capsule.

9. The medicated module of claim 1 where the secondary reservoir contains a liquid premix medicament.

10. The medicated module of claim 1 where the premixed medicament in the secondary reservoir comprises insulin and a GLP-1.

11. A drug delivery system to deliver two or more medicaments operable through a single dispense interface, comprising,
   a. a primary reservoir of medicament containing at least a first drug agent;
   b. a dose button operably connected to the primary reservoir of medicament;
   c. a single dispense interface configured for fluid communication with the primary reservoir; and
   d. a medicated module containing a secondary reservoir of premixed medicament containing at least one dose of the first drug agent and at least a second drug agent;
   wherein a single activation of the dose button causes medicament from the primary reservoir and at least one dose of the premixed medicament from the secondary reservoir to be expelled through the drug dispense interface.

12. The drug delivery system of claim 11 where the secondary reservoir contains a single dose of the premixed medicament.

13. The drug delivery system of claim 11 comprising a housing containing a single dose setter operably connected to the primary reservoir of medicament.

14. The drug delivery system of claim 11 wherein the first drug agent contained in the medicated module is of the same or an equivalent concentration as the first drug agent in the primary reservoir.

15. The drug delivery system of claim 11 where at least one of the primary reservoir and the secondary reservoir contains a liquid medicament.

16. The drug delivery system of claim 11 where the first drug agent in the primary reservoir comprises insulin.

17. The drug delivery system of claim 11 where the premix medicament in the secondary reservoir comprises insulin and a GLP-1.

18. A method of dispensing at least two medicaments from separate reservoirs, comprising, in combination, the steps of
   a. providing a drug delivery device comprising,
      a device housing containing a dose button operably connected to a primary reservoir of medicament containing at least a first drug agent; and
   b. providing a medicated module configured for attachment to the drug delivery device comprising, a secondary reservoir housing containing at least one dose of a premixed medicament containing the first drug agent and at least a second drug agent, where the module housing has mounted therein at least one needle;
   wherein a single activation of the dose button causes medicament from the primary reservoir and at least one dose of the premixed medicament to be expelled through the needle.

19. The drug delivery system of claim 11 where the primary reservoir is in fluid communication with the secondary reservoir.

20. The drug delivery system of claim 19 wherein the activation of the dose button causes medicament from the primary reservoir to flow into the secondary reservoir and thereby push out premix medicament from the secondary reservoir.

* * * * *